US009895163B2

(12) United States Patent
Trovato (10) Patent No.: US 9,895,163 B2
(45) Date of Patent: Feb. 20, 2018

(54) ACTIVE CANNULA CONFIGURATION FOR MINIMALLY INVASIVE SURGERY

(75) Inventor: Karen I. Trovato, Punam Valley, NY (US)

(73) Assignee: Koninklijke Philips N.V., Eindhoven (NL)

(*) Notice: Subject to any disclaimer, the term of this patent is extended or adjusted under 35 U.S.C. 154(b) by 941 days.

(21) Appl. No.: 12/439,840

(22) PCT Filed: Aug. 15, 2007

(86) PCT No.: PCT/IB2007/053253
§ 371 (c)(1),
(2), (4) Date: Mar. 4, 2009

(87) PCT Pub. No.: WO2008/032230
PCT Pub. Date: Mar. 20, 2008

(65) Prior Publication Data
US 2009/0248045 A1    Oct. 1, 2009

Related U.S. Application Data (60) Provisional application No. 60/825,629, filed on Sep. 14, 2006, provisional application No. 60/892,612, filed on Mar. 2, 2007.

(51) Int. Cl.
*A61B 19/00* (2006.01)
*A61B 17/34* (2006.01)
(Continued)

(52) U.S. Cl.
CPC ..... *A61B 17/3421* (2013.01); *A61M 25/0105* (2013.01); *A61B 17/3417* (2013.01);
(Continued)

(58) Field of Classification Search
CPC ........ A61B 17/3421; A61B 2017/3447; A61B 17/3417; A61B 2034/107; A61M 2025/0175
(Continued)

(56) References Cited

U.S. PATENT DOCUMENTS 5,788,713 A * 8/1998 Dubach et al. ............... 606/130
6,358,266 B1   3/2002 Bonutti
(Continued)

FOREIGN PATENT DOCUMENTS

DE    4223897 A1    1/1994
WO    2007059233 A2    5/2007

OTHER PUBLICATIONS

Webster, Robert J. et al "Toward Active Cannulas: Miniature Snake-Like Surgical Robots" Department of Mechanical Engineering. The Johns Hopkins University, Baltimore, Maryland, (2006).

*Primary Examiner* — Diane Yabut (57) ABSTRACT

The present disclosure provides for systems and methods for active cannula configuration. Active cannula systems include a plurality of telescoping, pre-shaped nitinol tubes configured and dimensioned to reach target locations within a particular anatomical region. A three dimensional image is read for the particular anatomical region. A series of arcs are generated between a point of the anatomical region and a target location. A pathway for the active cannula is calculated from the series of arcs. The pathway is used to configure and dimension the plurality of tubes. The active cannula system is adapted to reach relatively small and complex target locations.

17 Claims, 5 Drawing Sheets

(51) Int. Cl.
*A61M 25/01* (2006.01)
*A61B 17/00* (2006.01)
*A61M 25/00* (2006.01)
*A61B 34/10* (2016.01)

(52) U.S. Cl.
CPC ......... *A61B 34/10* (2016.02); *A61B 2017/003* (2013.01); *A61B 2017/00331* (2013.01); *A61B 2017/00991* (2013.01); *A61B 2017/3443* (2013.01); *A61M 25/0041* (2013.01); *A61M 2025/0175* (2013.01)

(58) Field of Classification Search
USPC ....................................................... 606/130
See application file for complete search history.

(56) References Cited

U.S. PATENT DOCUMENTS

| | | |
|---|---|---|
| 6,386,758 B2 | 5/2002 | Loser |
| 6,505,065 B1 | 1/2003 | Yanof |
| 6,572,593 B1 | 6/2003 | Daum |
| 7,993,351 B2 | 8/2011 | Worley et al. |
| 8,715,226 B2 | 5/2014 | Webster et al. |
| 2005/0159728 A1 | 7/2005 | Armour |
| 2005/0182295 A1 | 8/2005 | Soper |
| 2006/0129132 A1 | 6/2006 | Peterson |
| 2006/0229594 A1 | 10/2006 | Francischelli |
| 2009/0248045 A1 | 10/2009 | Trovato |

* cited by examiner

ACTIVE CANNULA CONFIGURATION FOR MINIMALLY INVASIVE SURGERY

CROSS REFERENCE TO RELATED CASES

Applicant claims the benefit of Provisional Application Ser. No. 60/825,629, filed Sep. 14, 2006.

The present disclosure relates to systems and methods related to active cannula designs and configurations that are customized for a patient to facilitate minimally invasive surgical procedures.

Existing navigation devices, such as catheters and bronchoscopes, have several disadvantages. A particular problem encountered in bronchoscope applications is that the bronchoscope typically has a relatively large tube diameter and can only turn or be otherwise navigated at the tip. The large size is partly due to the control mechanism built within the bronchoscope that enables it to turn. As a result of their size and lack of dexterity, conventional bronchoscopes are limited in their ability to reach certain regions. For example, a typical bronchoscope can only reach the center third of a lung, where the largest airways are located. This leaves two-thirds of all lung cancers (for example) unreachable with conventional bronchoscope technology and, therefore, untreatable without major physical intervention. Even a lung biopsy, which might distinguish a benign from malignant nodule, has over a 10% chance of causing lung collapse. Thus, potentially treatable diseases are often left untreated until the disease is so aggressive that surgery is warranted and/or required.

Catheters and guidewires associated with traditional surgical techniques are relatively flexible and can reach deep within the body by following vessels. However, these devices have a tip shape designed to address the most difficult of the likely turns within the anatomy. The device's ability to maneuver through only one type of challenging turn limits the applicability of the device. Often, catheters and guidewires are often used in an 'upstream' direction, where the vessel branching requires no specific control, saving the one difficult turn for a specific location. For example, insertion of a catheter into a distal artery, such as the femoral artery (used in balloon angioplasty) toward the heart means that vessels are joining in this direction, rather than dividing. While this is effective in many cases, there is no effective mechanism to traverse complex arteries as they travel with the blood as it flows away from the heart, or along veins leading away from the heart against the flow of blood. In the lung, catheters and guidewires have relatively little control at the distal end to reach specific branches of the lung, and are therefore not suited for reaching specific targets.

Insertion of a medical device such as a cannula, catheter, guidewire or scope (broncho, endo, etc.) can generally suffer from frictional issues and can cause tissue damage throughout the path traveled to a target. This can occur as the device is inserted into a designated anatomical region, especially when trial and error techniques through challenging anatomy cause a sawing motion. In addition, movement of the tool-tip during surgical or exploratory procedures cause motion to all of the tissue throughout the path. For example during biopsy, ablation, cautery, electrophysiology, etc., moving the tip of the device causes motion throughout the path of the device. This friction may dislodge vulnerable plaques leading to stroke, for example.

Prior techniques for moving an active cannula were primarily focused on the interaction of multiple nested tube shapes and strengths to create a characterizable motion at the distal tip. In order to use an active cannula by the sequential deployment of nested tubes, the configuration of the tubes must be defined so that the path can be achieved. It is not sufficient to find the midline through vessels, because this information does not describe how to break down the path into extensible, common sub-components. For example, an S shape cannot be deployed simply as a single, continuous S shape. This is because as one end emerges from the enclosing tube, it faces in the wrong direction. Rather, two C shapes must be nested so that the first rotates counter-clockwise and the second, oriented 180 degrees from the first, extends creating a clockwise C. Further, it would require custom fabrication into the shapes, such as by heating, if they were each slightly different. Further, the diameter of the tubes must match the proposed anatomy.

A technique has been previously disclosed describing how a path is defined for bronchoscope control to reach a given target in 3D, while also avoiding obstacles. This technique may also be applied to bendable catheters having a pre-determined preferred arc. Planning paths to a desired target with an active cannula has not been previously taught in 2D or 3D.

Active cannula systems may provide some benefits over existing access and navigation techniques including but not limited to the flexibility of the tubes associated with the active cannula system, the smaller diameter relative to other navigation systems, and the sequential extendable nesting design. The number of tubes in a particular active cannula series and/or system is limited by the diameter of the outer-most tube and whether the succeeding tubes fit within the anatomy as they are extended. As a result, some highly convoluted, narrow paths may still be difficult to reach using existing systems.

Accordingly, a need exists for an effective active cannula configuration system. These and other needs are addressed and/or overcome by the systems and methods of the present disclosure.

The present disclosure provides advantageous systems and methods for configuration of active cannulas for minimally invasive medical procedures. A customized tool called an Active Cannula (AC) is created for a specific patient based on a pre-acquired 3D image, and identification of a target location. An exemplary system according to the present disclosure includes a plurality of concentric telescoping tubes nested within each other. The nested tubes are configured and dimensioned to reach a target location by generating a tube pathway through a set of arcs resulting from a three dimensional image of a particular anatomical region. The requisite image is generally obtained using a three dimensional imaging system, wherein each arc is determined between an entry point on the anatomical region and the target location. The tubes are configured and dimensioned to reach relatively small and/or complex target locations within a particular anatomical region. The tubes may be advantageously fabricated from a material exhibiting desirable levels of flexibility/elasticity. Thus, one or more of the nested tubes may be fabricated from a nitinol material. The nitinol material has 'perfect memory', in that it can be bent when a force is applied, yet returns to the originally set shape once the force is removed. Nitinol can also be used within an MRI machine. It is a relatively strong material and therefore can be made thin walled, enabling the nesting of several tubes. Tubes with an outer diameter from about 5 mm down to around 0.2 mm are readily available in the market.

In an exemplary aspect of the present disclosure, the three dimensional imaging system can be a CT, Ultrasound, PET, SPECT or MRI, but may also be constructed from range sensors, stereo images, video or other non-medical imaging systems. Typically, the image of the particular anatomical region is used to configure and dimension each of the plurality of tubes to define a particular shape and extension length for each of the plurality of tubes. The defined shape and extension length of each of the plurality of tubes determines whether a target location is reachable. In an exemplary aspect of the present disclosure, the plurality of tubes is configured and dimensioned to pre-set shapes and extension lengths for a particular anatomical region. The pre-set plurality of tubes can include alternating curved and straight tubes.

In an exemplary system according to the present disclosure, the plurality of tubes are configured and dimensioned to pre-set shapes and extension lengths for a particular anatomical region associated with a particular individual. The tubes are configured and dimensioned to reach relatively small diameter locations and/or locations requiring complex maneuvers within the anatomical region. The anatomical region can be any desired region necessitating instrumental intrusion or procedure, including but not limited to thoracic regions, abdominal regions, neurological regions, cardiac regions, vascular regions, etc.

In an exemplary aspect of the present disclosure, the tubes are adapted to prevent tissue damage resulting from insertion friction by creating and/or providing a barrier with an outer tube of the plurality of tubes for those tubes nested inside. The tubes can further include a medical device member or other active structure at the tip of the furthest extending tube adapted to perform and/or facilitate a medical procedure at a target location. Medical devices associated with the present disclosure include, but are not limited to, catheters, telescopic tips, guide wires, fiber optic devices, biopsy, suture and curatage devices, and sensors (pH, temperature, electrical). Electrical sensors are more commonly used to examine cardiac electrical function for example. The tubes can be adapted to allow manual guidance and control over the insertion of the tubes into the anatomical region aided by tactile or visual feedback. Positional feedback can also be used such as electromagnetic tracking coils embedded in the tubes or within the payload carried by the tubes. This position can be displayed on a graphical display, preferably registered to an image.

The present disclosure further provides for a method for active cannula configuration including the steps of: (a) reading a three dimensional image of a particular anatomical region; (b) generating a series of arcs from a particular position and orientation in the three dimensional image; (c) calculating a pathway between an entry and target location using the generated series of arcs passing through the point; and (d) generating a plurality of concentric telescoping tubes nested within each other configured and dimensioned to reach the target location using the generated.

Additional features, functions and benefits of the disclosed systems and methods will be apparent from the description which follows, particularly when read in conjunction with the appended figures.

To assist those of ordinary skill in the art in making and using the disclosed systems and methods, reference is made to the appended figures, wherein.

The present disclosure provides for an active cannula configuration system and method that generates an active cannula customized to a patient and/or anatomical region-of-interest enabling minimally invasive surgical procedures to reach particular target locations that are commonly difficult to reach by traditional surgical means. Nitinol tubes allow for flexibility and dexterity to reach complicated and challenging target locations. One or more 3-D images are used to generate a series of 3-D paths that define the shape and extension length of the flexible tubes. In an exemplary aspect of the present disclosure, tube paths are computed within a few minutes. Configured AC systems and methods allow for complex vasculature to be traversed faster than manually shaped catheters that typically require trial and error to be formed correctly.

The motions required to reach a target are designed into the tool so it can perform multiple turns without the additional size or weight of motors, control wires, etc. This miniature, dexterous tool can provide accurate, minimally invasive reach into very small anatomical areas and/or regions.

According to the present disclosure, active cannula systems may include a plurality of telescoping, pre-shaped tubes. Concentric telescoping tubes made from flexible nitinol (nickel-titanium alloy), or other suitable material, are generally extended along an anatomical region, each tube having a particular curvature. Nitinol is a particularly desired material for cannula fabrication due to its memory attributes and flexibility, thus enabling a tube to conform into a larger tube surrounding it until the tube is extended. Typically, the largest tube is first introduced into a desired region followed by the introduction/extension of successively smaller tubes to an expected length and orientation. In an exemplary aspect of the present disclosure, tubes may be made of rubber or plastic which is less expensive but may require thicker walls. This may be preferable if the number of tubes required is sufficiently small that they can reach the target position, or the anatomy is large enough to accommodate each tube. The characteristics of their elasticity is also important, therefore it may be advantageous to nest them near to the time that they are deployed so they have less chance to take on a new shape.

An exemplary active cannula (AC) typically can have a plurality of telescopic nitinol tubes (often referred to as a series of tubes) operable to reach into relatively small and/or complex locations in a desired anatomical region.

According to a beneficial aspect of the present disclosure, an AC system may include a "standard set" of tubes alternating between curved and straight tubes. Using the "standard set" allows for reaching various locations within a given anatomical region without the cost or delay of custom manufacturing of each particular tube.

According to an aspect of the present disclosure, there is provided an exemplary method for configuration of an AC system. A particular 3-D image of a target anatomical region may be generated via an imaging system such as CT, Ultrasound, PET, SPECT, MRI, or other imaging means. The images, in an aspect of the present disclosure, may be registered to each other, creating a multi-modal image, such as, for example, PET-CT, where the PET provides critical information on the target lesions and the CT image can be segmented to define forbidden, 'critical regions', where the Active Cannula may not travel. A point, typically the target, is first defined. A point can also potentially be an entry or a central key point. Starting at a point, reachable locations are calculated and a correct set of telescoping tube shapes required to reach the 3-D target locations are determined. Based on such determinations, the individual tubes are selected and/or generated.

In the following sections, key components of a framework will be described and then specified for the active cannula application: a discretized configuration space, forbidden states, start or goal state(s), neighborhood and cost metric.

1. Configuration Space:

The configuration space is defined by the span of possible parameters that describe the state, sometimes called the 'configuration' of the device. For example, a robot configuration can be defined by the angle value of each joint. The span of all possible joint angle configurations forms the configuration space. Similarly, a vehicle's configuration can be specified by its x,y position and orientation. At each state, often an array entry specified by the parameter values for one device configuration, several values are stored, including the direction to proceed from this state to the next and the remaining cost to reach the goal from this state. These values are assigned by a search method, performed later.

The configuration of an Active Cannula (AC) may be represented by the x,y,z location and rx,ry,rz orientation of the AC's tip, resulting in a 6 dimensional problem space. Relevant locations may occur within an exemplary 512× 512×295 pre-procedural CT image, with exemplary x,y,z resolutions of 0.078, 0.078 and 0.3 respectively. Discretizing all orientations at 10 degree increments for the CT image would require 3.6 trillion states, each containing about 40 bytes, for a challenging memory requirement of 144 terabytes. After the remaining four components are explained, the technique is explained that enables the use of a configuration space that is on the order of the size of the 3D CT image.

Figure 7:
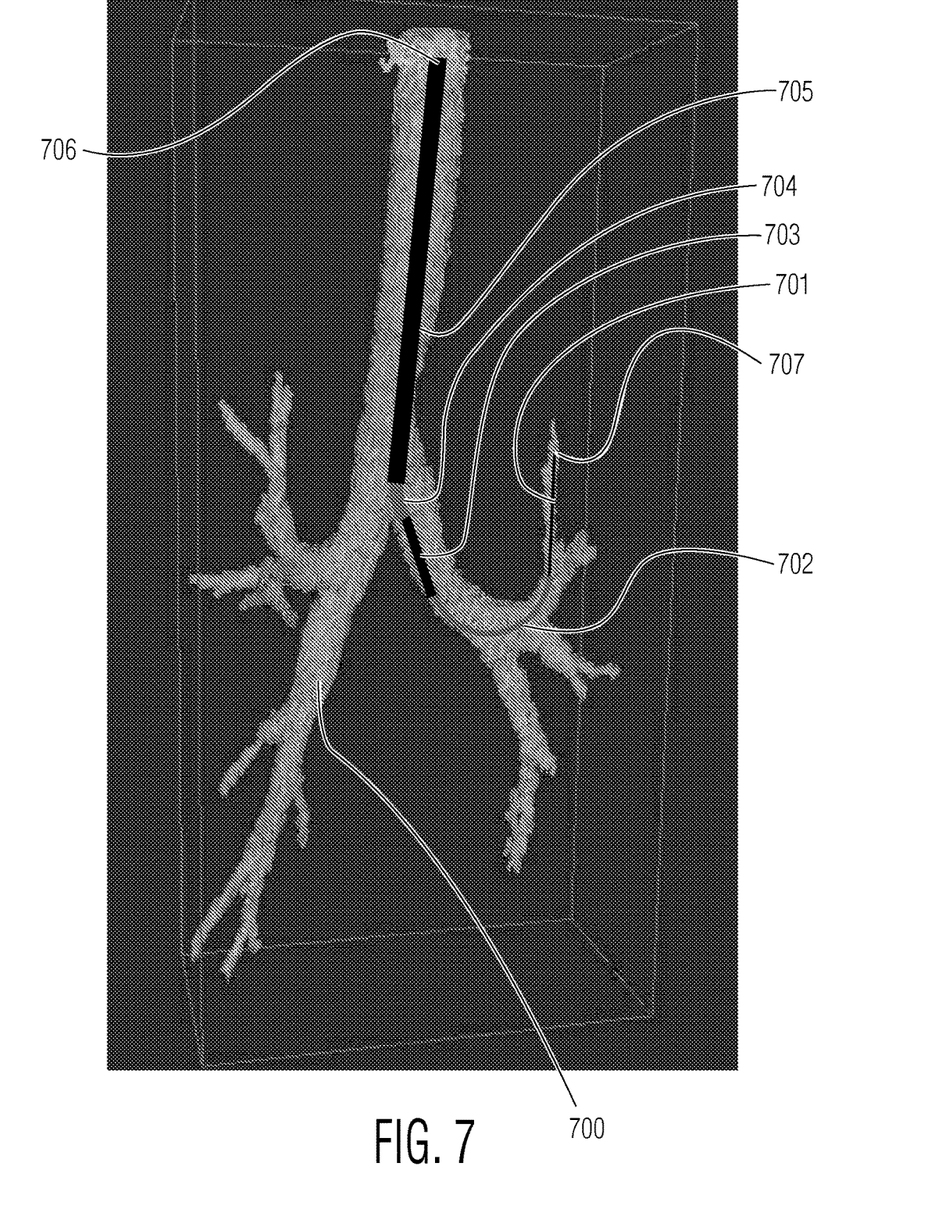
FIG. 7 illustrates a segmentation of lung air passages and an exemplary configuration of tubes associated with the present disclosure.

2. Forbidden States:

The anatomy is segmented so that some voxel regions are considered "free-space" states and others are forbidden regions through which the device must not pass. This segmentation step can be performed by many different techniques, including manual drawing, model based segmentation where the user places a nominal model in the area of the anatomy and a computer refines the segmentation, or fully automated segmentation. In this example, configuring an active cannula for the lung requires segmentation of the lung airways. The example image in FIG. 7 is segmented using a semi-automated Fast March (A*) method with a threshold. This generates an interior free-space volume, and an external forbidden volume (lung tissue).

3. Start or Goal State(s):

The x,y,z location of a tumor or other target (goal) can be selected as a seedpoint for the search (described later). Alternatively, the entry position such as a state within the trachea can be used as a seed point for the search. An orientation (rx,ry,rz) must also be defined for the seedpoint location(s).

Figure 8:
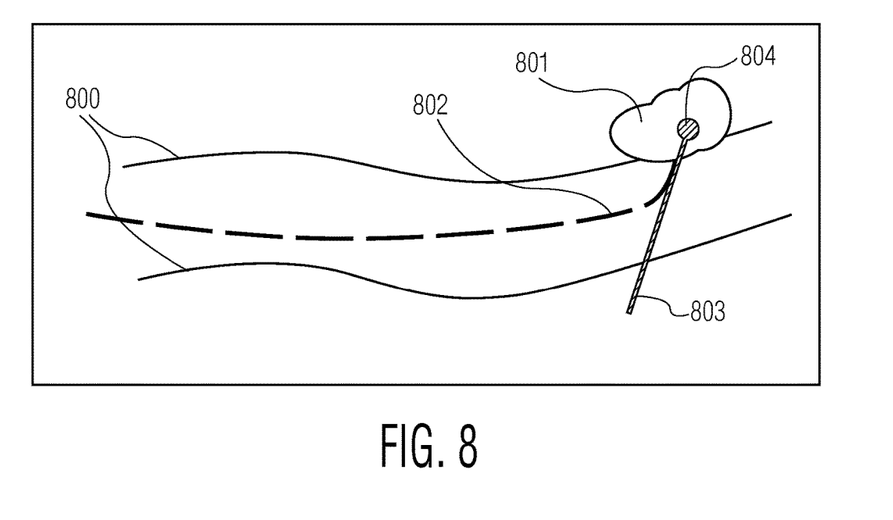
FIG. 8 illustrates an exemplary approach angle to a lesion intended for biopsy.

In a preferred aspect of the present disclosure, the start or goal is selected based on where the relative freespace is smaller (more constrained). From this location an entry angle is defined that is clinically suitable. For example in FIG. 8, airway 800 contains a lung nodule or suspicious mass 801 targeted for biopsy. The objective is to find a path 802 that penetrates the central area of the lung nodule or suspicious mass 801, reaching the target state 804 where the angle of insertion, also called the target approach angle 803, should be somewhat perpendicular so that the force of the needle at the puncture site is directed inward. In this case, the preferred angle may be a compromise between the ideal perpendicular to the surface but addressing the constraints of the limited vessel size by angling toward the larger airways (to the left) from which the active cannula will arrive.

Figure 9:
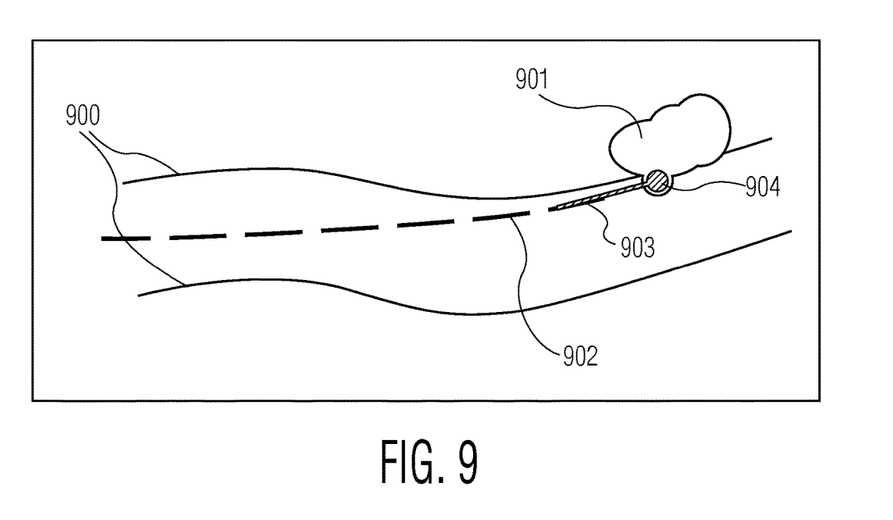
FIG. 9 illustrates an exemplary tangential approach angle to a lesion intended for Broncho Alveolar Lavage (BAL).

In other situations such as in FIG. 9, in an airway 900 the target approach angle 903 can be more tangential, possibly not even touching the surface of the lung nodule or suspicious mass 901 to the target state 904. This may be clinically useful such as when performing a Broncho Alveolar Lavage (BAL), in the lung for example. The target state 904 is reached via the proposed path 902. BAL is a process of infusing and reaspirating sterile saline solution (typically 0.9%) in distal segments of the lung via a fiber optic bronchoscope. The solution fills the airspaces distal to the tip of a bronchoscope. The reaspirated solution can be used to differentiate malignant from benign nodules identified on CT by assessing the aspirated cells. However, the sensitivity of this procedure varies, meaning actual disease may not be detected. One possible reason for this variable sensitivity is that the tip of the bronchoscope cannot reach sufficiently far into the lung, therefore more fluid than necessary is used to fill the distal area, reducing the chance that actual diseased cells are detected. If an Active Cannula is used, and a smaller portion of water is used, suspicious cells may be detected more easily because they will be present in a higher relative concentration. After a bronchoscope BAL procedure, fluid remains and must be absorbed by the lung or expectorated. After an active cannula BAL procedure, presumably less fluid will be used, causing fewer post procedural side effects. Finally, if the AC reaches more specifically to a target location, then the results may not only indicate disease, but will confirm the location.

4. Neighborhood:

The neighborhood encapsulates the set of fundamental device motions that can be performed in free space based on the available controls and mechanical properties of a device. The curvature for a particular tube has a specified 'minimum turning radius', similar to a car. In the example shown in FIG. 1, three different curvatures are considered for the Active Cannula. The first curvature 101 is straight (no curvature, or equivalently, infinite turning radius), the second curvature 102 has a 28 mm turning radius and the third curvature has turning radius of 14 mm. The series of points shown along curvature 102 for example demonstrate the position in X,Y space for a particular extension of the 28 mm curved tube. The tangent of this position gives the orientation. For an AC, the primary controls are rotating and advancing each of the tubes, where the curvature of each tube is pre-selected from among a set of discrete curvatures such as the three described in FIG. 1.

Figure 1:
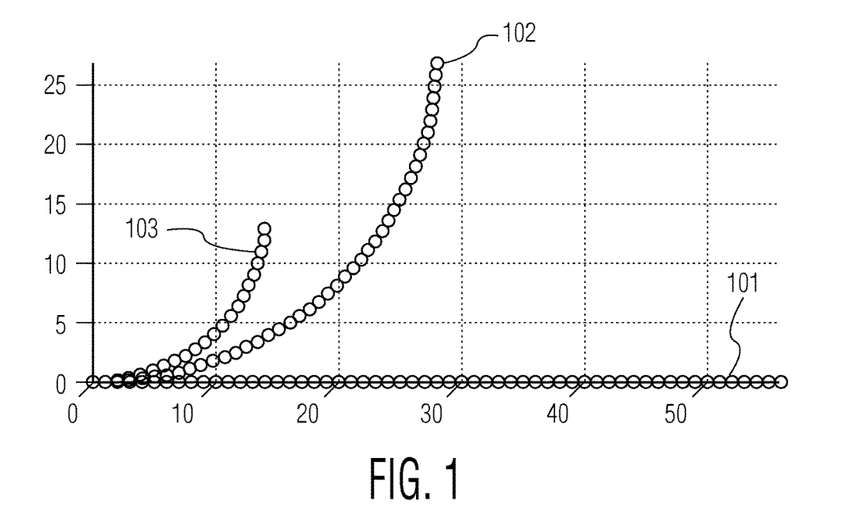
FIG. 1 illustrates three different exemplary cannula curvatures, 28 mm radius, 14 mm turning radius and straight (infinite radius)
Figure 2:
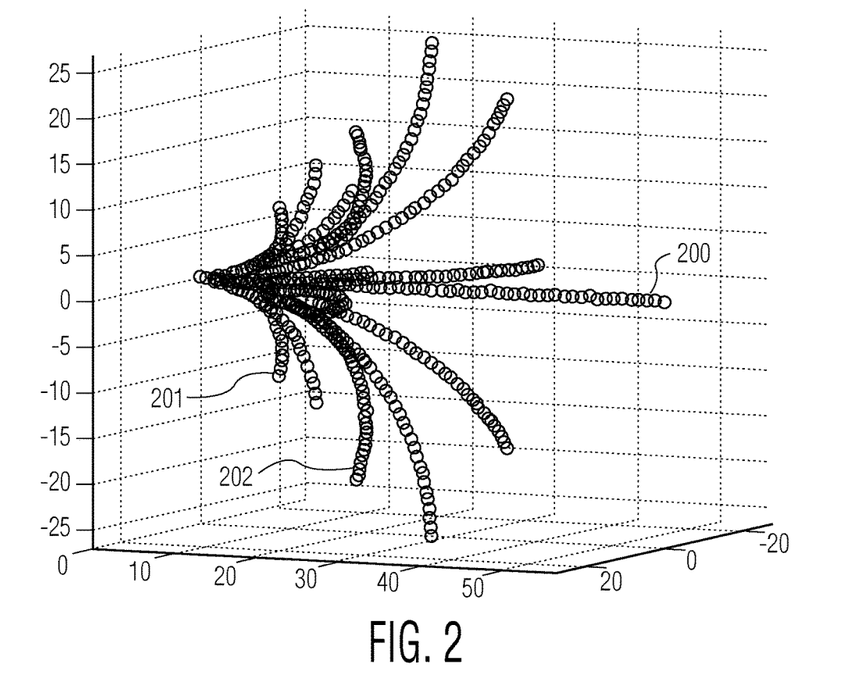
FIG. 2 illustrates an exemplary 3-D neighborhood of arcs, representing options of travel for the center of each tube associated with the present disclosure.

By rotating each of the three arcs illustrated in FIG. 1 in 45 degree increments, the resulting neighborhood can be illustrated as in FIG. 2. Each curved tube at a specific rotation is sometimes also called a fiber. In FIG. 2, there are eight rotations for the two curvatures (14 mm and 28 mm turning radius) illustrated, plus an additional option (straight with no rotation). One example is highlighted for each curvature, a 14 mm turning radius fiber 201 and a 28 mm turning radius fiber 202, for the same rotation. Each of the fibers can be extended to any length, following the same curvature. The length of the arc for a non-holonomic problem with an arbitrarily discretized space performs advantageously if a curved fiber is extended until the orientation is changed by 90 degrees, as for example shown in FIGS. 1 through 6. The straight portion of the neighborhood 200 ignores the rotational component and assumes that the incoming rotation maintains the same, since a straight tube at an arbitrary rotation follows the same path. It is noted that although FIG. 1 and FIG. 2 appear to have rectangular pixels, it is but a byproduct of the selection of axis markers.

The neighborhood for the active cannula is the mechanism that encapsulates the non-holonomic behavior of the device. Non-holonomic means that specific values for the control parameters (advancement plus rotation) do not uniquely define a resulting position and orientation without knowing characteristics of the path already taken. The neighborhood is a key component of a search (desribed later) because it captures the set of permitted motions from a location.

5. Cost Metric:

For each of the neighborhood states, a cost is assigned. This is the constituent cost for a local move based on the overall optimization criterion. In the active cannula example, it is desired to minimize the distance traveled. Therefore, the distance traveled along the arc or straight path from a home location to a neighbor defines the cost.

Turning now to the conversion of 6D to 3D configuration space for tractability, the discretized configuration space above, requiring 144 terabytes not only causes a memory problem on most computers, but in the next section, requires a search through these states. Proceeding with this framework requires a modified technique that reduces the configuration space and computation time.

Two observations drive this modification. The first is that the forbidden region derived from the 3D CT remains the same regardless of the orientation of the tip. It is therefore useful to identify conditions under which the 3D orientation can either be ignored or reduced to a few values stored per state, within the 3D space.

The second observation results from reviewing the primary objective of the configuration space, which is to store the values describing the current state and provide directions to the next state. If an orientation can be fixed at either the start or the goal seed location, this provides an anchoring basis for calculating unique, neighboring orientations. From this seed position and orientation, positions with specific orientations can be calculated for all reachable points.

Planned orientations rx,ry,rz can then be stored as values within each x,y,z configuration state along with cost and direction. Eliminating them as independent parameters of the configuration space, reduces the space from 6D to 3D, dramatically reducing the storage space required to about 77 million states and a more tractable 3 gigabytes of memory.

Positional (X,Y,Z) discretization error can also be reduced by storing the planned values within each state. The inherent (default) value of the discrete state is the value represented at the center of the voxel. Depending upon the level of discretization of the voxel, this value may be sufficient for controlling the proposed device. This may be further improved by optionally storing the precise positional (X,Y,Z) values within the state rather than incurring the discretization error throughout the configuration space. There are two specific advantages to this.

The first is that the location can be stored to arbitrary precision for the position. This can be particularly helpful when the dimensions of the voxels are not equal, which cause high precision in some directions (e.g. X and Y) with lower precision in other directions (e.g. Z). For example in a medical image such as in a CT, the voxels may be non-square or more properly, non-cubic or anisotropic, where the X and Y voxel length may be (0.078 mm) and the Z voxel length (0.3 mm). Although the obstacle coverage is defined with a resolution of voxels, the control can be more precisely defined by storing the computed, perhaps double precision, x,y,z,rx,ry,rz values within each state space.

The second is that if the current state is not adequately controllable to the next state, then this may be identified and automatically trigger alternate control strategies. In the simplest case, the device may stop and may wait for the proper, safe conditions to resume motion. For example, while a patient is breathing the x,y,z of the actual position of the device will move. We may decide that only when the actual position is within 0.5 mm of the planned scenario, then device control may proceed.

Once these key components are defined, the shortest, collision-free path can be generated from a fixed seed (start or goal) based on the set of available component tube curvatures or shapes and motions permitted with that tube (such as rotation and extension) which are encapsulated in the neighborhood. The path consists of concatenated arc or straight motions between the start and goal, and is carried out step-by-step with associated controls.

Concerning path generation, an A* search method may preferably be used to find all possible paths from the seed location(s). The 3D search has been described in, for example, prior applications including for vehicle maneuvering and bronchoscope maneuvering. The same 3D search is performed for the Active Cannula, but will be illustrated in 2D due to limitations of the paper medium.

Figure 3:
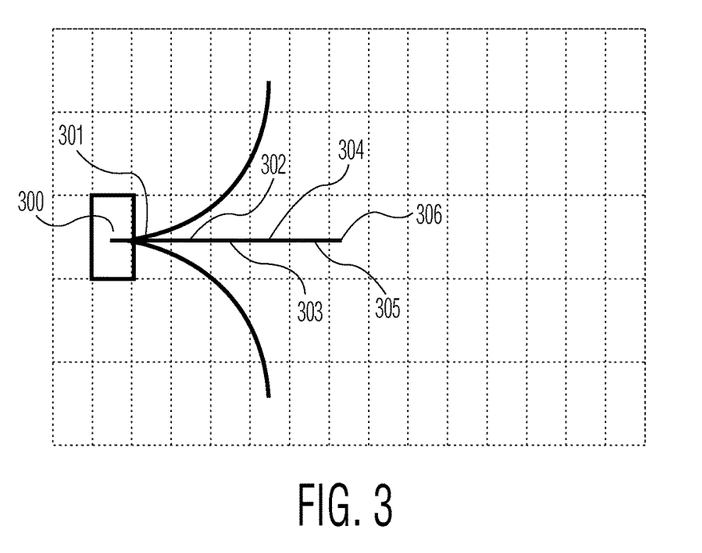
FIG. 3 illustrates an exemplary 2D neighborhood of arcs highlighting the neighbor arcs in the straight direction.
Figure 4:
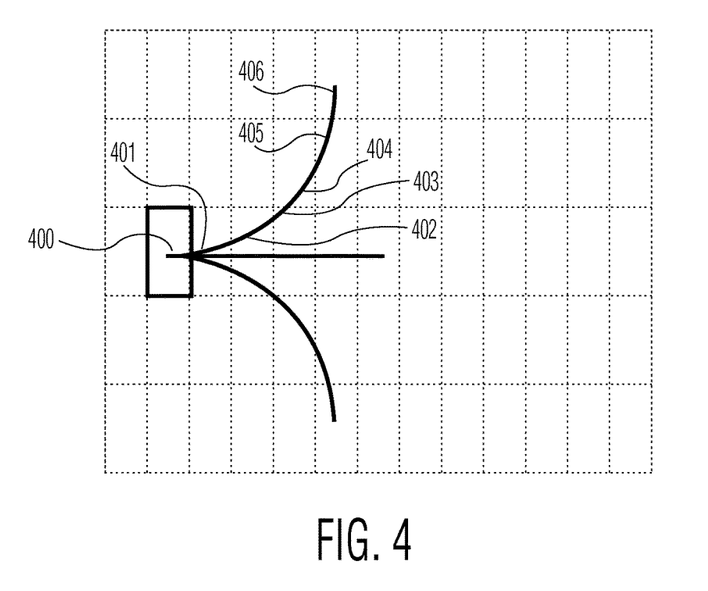
FIG. 4 illustrates the exemplary 2D neighborhood of arcs of FIG. 3 highlighting the neighbor arcs along a fixed curvature to the left.

FIG. 3 shows an exemplary 2D neighborhood. This simplified neighborhood shows a 'home position' 300 and a straight thread, including neighbors 301-306. There are also two threads having the same curvature, conveniently set at 180 degrees rotation from one another so that they lie on the same plane of the paper. In FIG. 4, the home position 400 corresponds to the home position 300 in FIG. 3, and neighbors along the left thread are identified 401-406. An equivalent set could be identified along the right thread.

Figure 5:
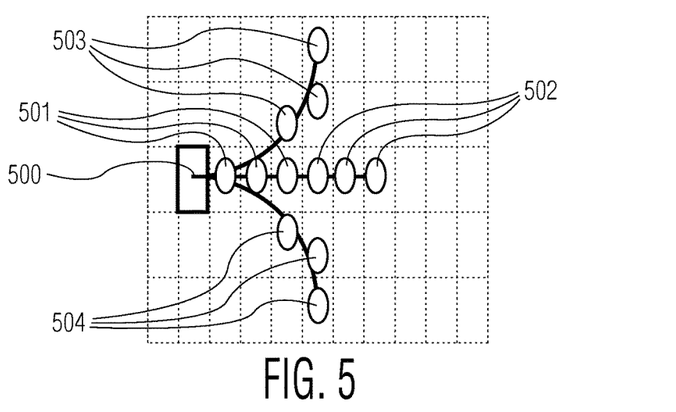
FIG. 5 illustrates the exemplary 2D neighborhood of arcs of FIG. 3 identifying the optimal neighbors from each fiber of the original set.

The neighborhood governs the locations considered as subsequently reachable neighbors, rather than considering only those that are adjacent. The states are expanded sequentially in a least-cost-first manner, adding the transition cost to the total cost so far, and storing only those that are minimum. The revised tip orientation is calculated based on the prior orientation and the change incurred by traveling to the selected neighbor. In FIG. 5, the neighbors ultimately reached with a minimum distance metric are shown. The neighbors reside in a non-cubic configuration space, which further highlights how a minimum cost to a state is identified. In this case, the neighbors comprised of 501 and 502, are reached via a straight path. The neighbors reached along the left fiber where there is not a more optimal (e.g. straight) path to these states are identified as 503. Similar neighbors can also be identified along the right fiber as 504. These neighbors become open nodes for subsequent rounds of expansion.

Figure 6:
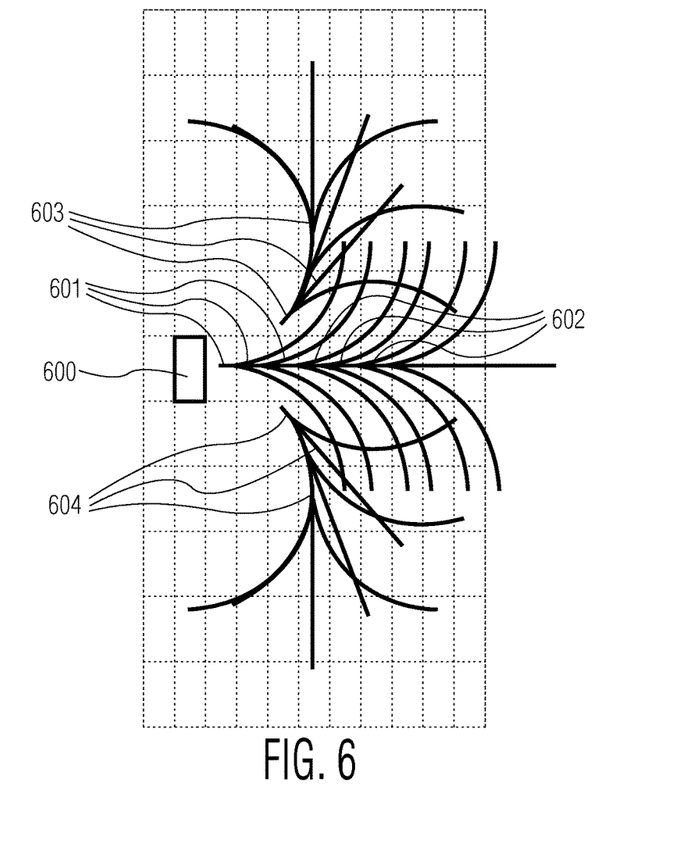
FIG. 6 illustrates coverage resulting from the expansion of a first set of opened neighbor arcs and concatenating of arcs.

In FIG. 6, the original home node 600 is shown, along with an illustration of the pattern of neighbors that would be expanded at the locations and orientations described in FIG. 5. At each 'open location', the home node 600 orientation is read, and the subsequent expansion is oriented with respect to that orientation. The positions and orientations of the set of open neighbors 503 from FIG. 5, are expanded at locations 603, with a new neighborhood oriented to match the open node's home orientation. Similarly, the open nodes of 501 and 502 of FIG. 5 are expanded at locations 601 and 602 of FIG. 6, and the open nodes of 504 in FIG. 5 are expanded at locations 604.

This simplified search example so far assumes there are no forbidden states. The expansion of a neighborhood is preferably performed from the home location of the neighborhood along each fiber from nearest to farthest. If a forbidden state is discovered, then the remainder of the fiber is considered unreachable and the search continues with the next fiber. This prevents the path from 'jumping over' a region that is illegal.

The same search technique, including the sequential search through the fibers to avoid obstacles is performed in 3D. It requires only that the neighborhood shown in FIG. 2 is re-oriented to a given position and orientation of an open node to calculate the set of subsequently reachable states. The process terminates when the successive computations either fill the space (when there are no more open states) or the search reaches another acceptable termination-state. A set of acceptable termination states for example may be any node along a plane of the uppermost trachea, when, e.g., the search starts from a target such as target state 804 of FIG. 8.

An intuitive analogy for this least-cost-first A* expansion follows. Imagine a wave generated by a pebble dropped in a pond at a seed location. As the waves ripple out, propagating around islands (forbidden regions) a snapshot is taken every second, including a timestamp ($t_0 \ldots t_n$). Drawing a perpendicular to the waves on the snapshots forms a 'pointer' that gives directions from every reachable location toward the source seed. From any reachable location, one needs only to follow the pointers from location to location to reach the seed location where the pebble was dropped. In addition, the timestamp on the image containing the current location indicates the estimated time required to travel back to the seed. Whenever a location is not reached by the waves, there is no path between this location and the seed location. Identifying situations that produce no viable path (using a specific device) is a useful property, since it saves time and energy in a needless struggle. When there is no path, other devices can be modeled to find one that is effective. Another approach is to identify whether one or more obstacles can be moved. Although this analogy is described in 2D, the A* method works as well in 3D or higher dimensions. Several efficient A* techniques not described here focus the search so that only the most likely states required for the solution are calculated.

With respect to path following, if a termination node is reached, then a path is computed between the termination node and the seed. Alternatively, a user or computer can select the end point to be connected to the nearest seed. The path is generated state to state, between the start and goal. Following from one state to another requires reading the 'direction vector' which might be stored as a neighbor number. As shown in FIGS. 3 and 4, the neighbor number also indicates the fiber, and therefore the type of path taken. For example, a neighbor located at 405 in FIG. 4 identifies that a specifically curved arc was directed left a particular distance, resulting in a particular location and orientation. This corresponds to the rotation within the enclosing tube and insertion length required for this curved tube to reach the next state along the path.

In FIG. 7, an example path is shown between the entry at 706 and the target 707. In order to calculate the number of tubes correctly, if a fiber leads to the same type of fiber (having the same relative orientation and curvature) along the path, it should be considered one continuous tube. In other words, arcs having the same curvature and relative rotation can be concatenated to become a longer tube with the same specification, for example two 28 mm radius arcs at +45 degrees rotation. Each change in thread type in the series represents a change to the next tube in the nested series of tubes of the AC system. The path given in FIG. 7 is a schematic in order to simplify the visual results. It is noted that the tube must pass through the nose or mouth to reach the trachea and consider the path from the entry point 706, which has a specified orientation.

The first tube is straight and must advance the length of 705. From this point a second tube 704 is advanced until it reaches where 704 connects to tube 703. This second tube 704 has a narrower outer diameter than the inner diameter of 705 and has a curvature specified by the neighbor and fiber selected. In a similar fashion, 703 is straight and extends until it reaches 702, and 702 is curved, extending until it reaches 701. Each successive tube is smaller than its predecessor.

Regarding defining tube radius for a particular function and anatomy, a path is viable only if the series of tubes can actually fit inside a specified region. A challenge is that anatomy can be complex, varying in diameter throughout. Also, the more types of maneuvers required, the more tubes are required, and the larger diameter required at the entry. Three methods are presented to generate tube diameters based on the given path and free-space available. This is followed by a fourth, which is a preferred method of the present disclosure.

1. The brute force method is to create the path, and compute the required tube outer diameters for each section of tube, starting from the smallest. For each point along the path, test for illegal states between the point and a radius distance. If there is an intersection, the path is not viable, however without some additional methods this leaves the viability to luck.

2. The very safe method is to shrink the free-space by the size of the largest tube expected. In this method, every path can be realized because it is within the boundaries. Unfortunately it will also cut off access to anatomy that could be reached by small tubes.

3. The optimist's method is to shrink the free-space by the size of the smallest available tube's outer diameter. This immediately delineates the regions where no access is possible even with the smallest tube, and regions of free-space that continue to offer some potential. Planning in this space improves the chances of identifying a viable path, but still does not guarantee it.

4. An exemplary preferred method has several key steps:
    4.1—Pre-compute several versions of the forbidden region. Each forbidden region is shrunk by the outside radius of each useful tube. A tube is useful only if it nests with the other tubes and the smallest is large enough to carry the intended payload or tool. The intended use of the active cannula determines the smallest useful tube. For example, if a camera is to be inserted, it will be larger than if a fluid sample is to be taken and the tube is empty. Shrinking free-space, or equivalently, region growing the forbidden space, can be performed rapidly, and only once for each useful tube.

4.2—Choose the seed within a narrow part of the anatomy along the path. In the lung therefore, a preferred seed is likely to be a distal tumor location rather than the center of the esophagus. In the brain, the narrowest vessel should be chosen, such as an ophthalmic artery rather than the carotid artery for example. Although this is typically located at the target, it is possible to be between the target and the entry point such as in a vascular application where there is plaque buildup midway.

4.3—Set the forbidden region at the seed to be determined by the outer radius of the smallest useful tube.

4.4—Track the total number of tube changes that have occurred since the seed location. This can be stored in the configuration space in addition to the cost-to-goal. When a node is expanded, the forbidden region is selected based on the number of tube changes, which defines the radius of the current tube used.

When a terminating node is reached, the radius of the required tube will also be specified. The use of an AC system according to the present disclosure allows clinicians and/or other medical personnel to reach/access relatively small diameter target locations and/or target locations requiring complex maneuvers within a particular anatomical region.

Active cannula technology offers several advantages over other navigation devices including, but not limited to: (i) effective control and angulation of a telescopic tip without the use of joint motors or marionette wires; (ii) smaller tube diameter than traditional devices; (iii) cannulas that are relatively inexpensive and typically disposable; (iv) nitinol and similar fabrication materials allow for cannulas to be formed into arbitrary shapes and curvatures, thus facilitating entry and/or access into complex regions; (v) nitinol is an MRI friendly material; (vi) pre-formed cannula configurations can be guided manually with the assistance of image guidance and later controlled by MRI friendly piezo-motors; (vii) successively smaller concentric cannulas match various shapes for use in various medical applications which enter a larger region and ultimately reach to successively smaller regions; and (viii) early deployment of a cannula system can be achieved with manual control and accurate calculations of configurations.

According to an illustrative aspect of the present disclosure, a standard set of cannulas can be defined such that a plurality of targets, a lung for example, can be reached using particular pattern of tubes but custom deployed at particularly calculated angles and lengths for a particular patient and/or target location. A series of arcs and straight tubes can be calculated that reach a particular target location. Target tube paths are generated from the resulting series of arcs and straight tubes. The path calculation may be weighted such that a change from one arc to another incurs an additional penalty.

In another illustrative aspect of the present disclosure, custom shaping of nitinol tubes may be avoided by careful selection of a predefined set of tubes. In an exemplary system, tubes can be nested in either a set of fixed arcs, or in an alternating set of arc-straight-arc-straight tubes. Preparing appropriate predefined sets allows for simplified and speedy path calculations. Moreover, standard sets of cannulas can be produced in massive quantities rather than requiring custom shaping and manufacturing. Having a pre-set pattern enables the potential reuse of the same AC system extended to different lengths to reach different target locations in the same individual in the same procedure. Predetermined shape and extension distance patterns for a particular patient can significantly reduce costs associated with a particular medical procedure. Further, manual deployment provides the ability for a technician/clinician, such as a surgeon, to provide physical guidance and control over the insertion process aided by tactile, visual, location or other types of feedback. Particular steps can be taken to facilitate accurate manual deployment including but not limited to:

a. etching distance markings into the tubes so that a precision distance can be deployed at each motion;

b. etching orientation markings into the tubes to enable the proper orientation of the tubes;

c. in a particular situation where a fixed set of shapes are required and the cannula is not intended to be used for a different target location, the tubes can have an interlocking ridge to lock the proper orientation relative to each tube; and d. tubes may be cut to the proper length so that each successive tube terminates at the same location as the larger (parent) tube.

The number of tubes associated with an exemplary AC system is limited by the diameter of the outer most tube. Particular steps can be taken to facilitate minimizing the number of tubes used to reach a target location in a particular anatomical region including but not limited to:

a. adding a handicap within the calculation methodology for each new arc type or orientation causes a feasible pathway to occur, while reducing the total number of tubes and/or customized tubes required.; and b. including a highly flexible catheter, guide wire, and/or fiber optics to the end of the last extending tube to reach the farthest most complicated target location.

Exemplary AC systems and methods can be used for a variety of medical, diagnostic and/or surgical applications, including lung cancer diagnosis/biopsy and the like. For example, an AC system can be used to perform a biopsy using image guidance and tracking for precision delivery of biopsy tools. An AC system according to the present disclosure facilitates autofluorescence by using image guidance, tracking and fiber optic transmission and sensing. Indeed, exemplary AC systems and methods associated with the present disclosure can be utilized in lung cancer therapy for reaching target locations beyond current practice.

Exemplary AC systems and methods according to the present disclosure may also be useful in photodynamic therapy (PDT). PDT is already clinically approved and reimbursed for lung carcinoma. In an exemplary PDT procedure, an agent (e.g., Photofrin®) is injected 24-72 hours prior to therapy, accumulates at cancer sites, and is activated by light delivered within 1 cm of a lesion. Unfortunately, bronchoscopes only reach the largest passages, representing about 33% of the lung. The smaller passages, where oxygen exchange occurs, cannot be reached (or reached accurately) by current techniques, systems or methods. An AC system according to the present disclosure allows for reaching relatively smaller target locations through the use of high-resolution images and tracking. In an exemplary aspect of the present disclosure, an AC system according to the present disclosure may work in conjunction with current bronchoscope practice.

Exemplary AC systems can be utilized for biopsy of hard to reach anatomical regions to determine the extent and/or need for molecular therapy or other intervention. It can also be utilized for 'on the spot' delivery of electronically generated radiation, e.g., using Xoft's Axxent miniaturized 2.25 mm X-ray source. In a cardiac environment, an exemplary AC system associated with the present disclosure can be useful in accessing difficult locations or orientations. For vascular applications, an AC system according to the present disclosure can reach through complex vessels currently unreachable by existing medical techniques. Moreover, the risk of dislodging clots is reduced since nested cannulas produce friction only for a portion of the entry path rather than the entire distal length.

The present disclosure provides for AC systems that are also operable for minimally invasive surgeries for gallstones. The cannulas can be adapted to reach a gallbladder for removal. For gastroenterology, an exemplary AC system according to the present disclosure is adapted to deliver PDT to a particular GI tract and reach target locations previously unreachable. It is also possible to reach target locations into a brain through minimally invasive vasculature.

Although this example is given in 3D, clearly the solution works for 2D images as well, with 2D neighborhoods encapsulating the device's permitted motions.

Although the present disclosure has been described with reference to exemplary aspects, features and implementations, the disclosed systems and methods are not limited to such exemplary aspects, features and/or implementations. Rather, as will be readily apparent to persons skilled in the art from the description provided herein, the disclosed systems and methods are susceptible to modifications, alterations and enhancements without departing from the spirit or scope of the present disclosure. Accordingly, the present disclosure expressly encompasses such modification, alterations and enhancements within the scope hereof.

The invention claimed is:

1. An active cannula configuration system comprising:
a device adapted to generate a plurality of concentric telescoping tubes cooperatively configured and dimensioned to reach a target location relative to an anatomical region through a set of arcs, wherein each arc is determined between a point associated with the anatomical region and the target location, wherein the device is further adapted to define a configuration of the plurality of concentric telescoping tubes by components of a framework, relative to the anatomical region, that include a discretized configuration space that comprises a span of possible parameters describing a state of the plurality of concentric telescoping tubes represented by discrete quantities of both x,y,z locations and rx,ry,rz orientations of a tip of the active cannula, forbidden states, start or stop states that include an orientation defined for seed point locations, and neighborhoods which encapsulate sets of fundamental motions of the active cannula that can be performed in free space based on its available controls and mechanical properties, further wherein responsive to the defined components, the active cannula configuration system is adapted to generate a shortest collision-free path from a seed point location based on (i) a set of available component tube curvatures or shapes and (ii) motions permitted with a corresponding tube that are encapsulated in a given neighborhood, wherein generating the shortest collision-free path includes using a search technique to compute all possible paths from the seed point location in the given neighborhood, wherein each respective neighborhood governs locations and orientations considered as subsequently reachable neighbors along corresponding tubes, wherein neighbors become open nodes for subsequent rounds of expansion, wherein the locations and orientations of the open nodes are expanded with a new neighborhood oriented to match a corresponding node's home orientation.

2. The system according to claim 1, wherein a start point is selected based on where a relative freespace within the framework, relative to the anatomical region, is smaller.

3. The system according to claim 1, wherein the plurality of concentric telescoping tubes comprises a pre-set plurality of tubes that include alternating curved and straight tubes relating to a particular anatomical region.

4. The system according to claim 3, wherein the particular anatomical region is associated with a particular individual.

5. The system according to claim 1, wherein the anatomical region is a lung.

6. The system according to claim 1, wherein the plurality of concentric telescoping tubes include a medical device member disposed at a tip of a furthest extending tube adapted to perform a medical procedure at a particular target location.

7. The system according to claim 1, further wherein expansion of a neighborhood is performed from a corresponding home location of the neighborhood along each tube from nearest to farthest, further wherein for any given tube, responsive to discovery of a forbidden state, a remainder of the given tube is considered unreachable, and searching continues with a next tube.

8. The system according to claim 7, wherein the active cannula system is still further adapted to perform three dimensional (3D) sequential searching through the tubes to avoid the forbidden states which are indicative of obstacles.

9. The system according to claim 1, wherein the plurality of concentric telescoping tubes comprise a predefined set of tubes further configured to extend to different lengths to reach different target locations in a same individual in a same procedure.

10. The system according to claim 1, wherein the framework further includes a cost metric, wherein cost is defined by a distance traveled along an arc or straight path from a home location to a neighbor within the given neighborhood, and further wherein the active cannula system is adapted to minimize the distance traveled.

11. A method for active cannula configuration comprising the steps of:
(a) obtaining an image of an anatomical region, via a three dimensional imaging system, the image including a discretized configuration space;
(b) generating a series of concatenated path shapes between an origin and destination within the image to form a pathway; and
(c) generating a plurality of concentric telescoping tubes operatively configured and dimensioned to reach a target location via the generated pathway, wherein generating the plurality of concentric telescoping tubes includes defining a configuration of the plurality of concentric telescoping tubes by components of a framework, relative to the anatomical region, that include the discretized configuration space which further comprises a span of possible parameters describing a state of the plurality of concentric telescoping tubes represented by discrete quantities of both x,y,z locations and rx,ry,rz orientations of a tip of the active cannula, forbidden states, start or stop states that include an orientation defined for seed point locations, and neighborhoods which encapsulate sets of fundamental motions of the active cannula that can be performed in free space based on its available controls and mechanical properties, the method further comprising generating, in response to the defined components, a shortest collision-free path from a seed point location based on (i) a set of available component tube curvatures or shapes and (ii) motions permitted with a corresponding tube that are encapsulated in a given neighborhood, wherein generating the shortest collision-free path includes using a search technique to compute all possible paths from the seed point location in the given neighborhood, wherein each respective neighborhood governs locations and orientations considered as subsequently reachable neighbors along corresponding tubes, wherein neighbors become open nodes for subsequent rounds of expansion, wherein the locations and orientations of the open nodes are expanded with a new neighborhood oriented to match a corresponding node's home orientation.

12. The method according to claim 11, wherein the plurality of concentric telescoping tubes alternate between straight tubes and curved tubes.

13. The method according to claim 11, wherein the tubes are configured and dimensioned to reach relatively small and complex target locations.

14. The method according to claim 11, further wherein expansion of a neighborhood is performed from a corresponding home location of the neighborhood along each tube from nearest to farthest, further wherein for any given tube, responsive to discovery of a forbidden state, a remainder of the given tube is considered unreachable, and searching continues with a next tube.

15. The method according to claim 14, further comprising:
performing three dimensional (3D) sequential searching through the tubes to avoid the forbidden states which are indicative of obstacles.

16. The method according to claim 11, wherein the plurality of concentric telescoping tubes comprise a predefined set of tubes further configured to extend to different lengths to reach different target locations in a same individual in a same procedure.

17. The method according to claim 11, wherein the framework further includes a cost metric, wherein cost is defined by a distance traveled along an arc or straight path from a home location to a neighbor within the given neighborhood, wherein the method further comprising:
minimizing the distance traveled.

* * * * *